(12) United States Patent
Bango et al.

(10) Patent No.: US 7,579,442 B2
(45) Date of Patent: *Aug. 25, 2009

(54) METHOD FOR STROMAL CORNEAL REPAIR AND REFRACTIVE ALTERATION

(75) Inventors: Joseph J. Bango, New Haven, CT (US); John B. Fenn, Richmond, VA (US)

(73) Assignee: Ocugenics, LLC, Orangevale, CA (US)

( * ) Notice: Subject to any disclaimer, the term of this patent is extended or adjusted under 35 U.S.C. 154(b) by 254 days.

This patent is subject to a terminal disclaimer.

(21) Appl. No.: 10/414,796

(22) Filed: Apr. 16, 2003

(65) Prior Publication Data

US 2003/0193118 A1 Oct. 16, 2003

Related U.S. Application Data

(60) Provisional application No. 60/373,725, filed on Apr. 16, 2002.

(51) Int. Cl.
*A61K 38/17* (2006.01)
*B29C 47/02* (2006.01)

(52) U.S. Cl. ...................... 530/356; 264/465

(58) Field of Classification Search ........ None
See application file for complete search history.

(56) References Cited

U.S. PATENT DOCUMENTS

| 4,505,855 | A | | 3/1985 | Bruns et al. |
| 5,222,663 | A | * | 6/1993 | Noakes et al. .......... 239/3 |
| 5,681,869 | A | | 10/1997 | Villain et al. |
| 5,955,438 | A | * | 9/1999 | Pitaru et al. .......... 514/21 |
| 2002/0090725 | A1 | * | 7/2002 | Simpson et al. ......... 435/402 |

FOREIGN PATENT DOCUMENTS

| WO | WO 0218441 | 3/2002 |
| WO | WO 0240242 | 5/2002 |

OTHER PUBLICATIONS

Reneker DH et al., Bending instability of electrically charged liquid jets of polymer solutions in electrospinning, May 2000, Journal of Applied Physics, vol. 87 No. 9, p. 4531-4547.*
The Meriam-Webster dictionary on-line version accessed at http://meriam-webster.com on Jul. 21, 2008; entry for the word 'duplicate' 2 pages.*
Merrett et al., IOVS papers in press May 30, 2008 30 pages.*

* cited by examiner

*Primary Examiner*—Anish Gupta
*Assistant Examiner*—Ronald T Niebauer
(74) *Attorney, Agent, or Firm*—James F. Kirk

(57) ABSTRACT

A method and means of providing stromal repair and improved refractive correction by creating corneal stromal collagen tissue with fibril diameter and spacing that duplicates the optical transmission and diffusion characteristics of natural corneal collagen. The repair method includes implanting the collagen scaffold during laser corneal ablation or other interlamellar surgery to improve visual acuity or to preclude the possibility of ectasia.

7 Claims, 7 Drawing Sheets

METHOD FOR STROMAL CORNEAL REPAIR AND REFRACTIVE ALTERATION

CROSS REFERENCE TO RELATED APPLICATIONS

This application claims patent priority of provisional Patent Application Ser. No. 60/373,725, filed Apr. 16, 2002.

In addition, Disclosure Documents Nos. 502428 and 503243 filed Dec. 7, 2001 and Dec. 29, 2001 respectively.

FEDERALLY SPONSORED RESEARCH

Not applicable

SEQUENCE LISTING OR PROGRAM

Not Applicable

BACKGROUND OF THE INVENTION

1. Field

This invention relates in general to corneal reconstruction and in particular to a method and means of regenerating a corneal lamella membrane in an effort to restore vision in patients suffering from failed Laser Corneal Ablation Procedure (LCAP) such as those described as LASIK or LASEK, radial keratomy, keratoconus, corneal abrasions, and trauma. Further, this invention holds promise as a method to devise a integral refractive correcting contact-like lens which can be implanted on top of or into the corneal stroma.

2. Prior Art

Corneal damage is a leading cause of impaired vision and blindness. Scarring due to chemical burns, missile damage, genetic disorders, radial keratomy, or failed LCAP are leading causes of corneal eye damage. In particular, failed LCAP is the most common source of vision loss due to corneal damage. Refractive complications can include too much or too little correction, or an imbalance in correction between the eyes. In some cases, patients who experience improper LCAP may be left near or farsighted or with astigmatism, necessitating spectacles or contact lens wear, or in severe cases, may be faced with blindness. Corneal inflammation is another side effect, which can cause a swelling known as diffuse interface keratitis, leading to corneal hazing, and ultimately, blurred vision. LCAP performed on certain patients with large pupil diameters, thin corneas, or keratoconus, leading to night glare, starbursting, haloes, reduced vision under dim lighting, blurring, or reduced overall visual acuity. At present, only corneal transplants or penetrating keratoplasty, are considered a viable treatment.

Given the enormous media attention given to LCAP, most individuals readily embrace LCAP as a cure-all solution to disposing of their glasses and contact lenses. However, all ophthalmologists readily admit, in their FDA-mandated informed consent that not everyone sees well enough after a LCAP procedure to truly eliminate their use of glasses and contact lenses. In fact, studies have shown that over 2 percent of LCAP patients experience degradation in visual acuity that was uncorrectable through refractive means. Of these patients, debilitating effects due to irregular astigmatism and double vision (due to corneal warping) were common. This is particularly troublesome since, unlike cataract surgery, which restores vision in defective eyes, LCAP is an elective process practiced on healthy eyes. While LCAP is certainly a preferable procedure over radial keratotomy, the success of the procedure and the coupling of medicine and marketing has caused in many patients, who should not have undergone the process to be largely forgotten. Further, intraoperative complications include decentered ablations and flap complications, such as a partial or lost flap.

Postoperative effects due to failed LCAP can include pain as a result of disturbance of the epithelial layer, displacement of the corneal flap, inflammation, or infection. Diffuse interface or lamellar keratitis, also known as 'DLK' or Sands of Sahara, is the most serious reaction and can produce corneal hazing, blurred vision, farsightedness, astigmatism, and permanent corneal irregularities. Another equally serious complication is keratoectasia induced by LCAP. Ectasia is the distension of the cornea due to an internal pressure gradient causing the cornea to steepen and distort. The most common side effects of LCAP are dryness of the eyes, night glare, starbursting, haloes, induced spherical aberration, induced coma, and reduced visual acuity. Previous attempts to correct the corneal structure to alleviate the aforementioned conditions have been hampered by the fact that only a fixed quantity of tissue is available for ablative modification. By its' very nature, laser ablation or LCAP removes healthy tissue, thus undermining the structural integrity of the cornea. Replacement tissue is not available due to the fact that no other part of the body has the specialized collagen fibril structure inherent in the cornea.

The most widely practiced means of corneal repair has been the corneal transplant. However, problems of tissue rejection, of immunosuppressive medication, gross refractive errors, and limited supplies of suitable donor tissue hamper transplants. While numerous experiments have been conducted in an effort to create laboratory-grown corneal tissue in vitro, the drawback of most of these methods is that they attempt to generate only one type of corneal cell structure, such as the epithelial or endothelial layers. Stromal creation in the laboratory has in the past been met with limited success since no means have been found that successfully form the delicate collagen fibrils with micron sized diameters and fibril spacing necessary for corneal transparency and diffusive permeability.

Many prior art techniques rely on implanting a polymer of material (other than collagen or collagen that is devoid of fibrils), thus lacking in permeability as well as transparency inherent in native tissue. For example, U.S. Pat. No. 4,505,855 to Bruns and Gross issued Mar. 19, 1985, describes the fabrication of a non-fibrilized collagen button produced by ultracentrifugation for transplantation. This concept suffers from the fact that the lack of a controlled fibril diameter and fibril organizational structure significantly hinders the osmotic pumping of proteins and aqueous media through the fabricated collagen region. The same holds true with gaseous diffusion. As a result, transparency will be impaired. Further, since the collagen button is designed to replace only the damaged corneal stroma, leaving out other vital tissues (the stroma is responsible for 90% of corneal thickness, composed of collagen fibrils and is the principal supportive structure of the cornea. Covering the stroma is the epithelium, a cellular membrane about 5 layers thick, below which is the Bowman's Layer, a thin layer separating epithelium and stroma. On the anterior portion of the stroma is the endothelium layer, responsible for dehydrating the cornea via a sodium-potassium pump mechanism and to maintain corneal optical clarity. Last is the Descemet's membrane, which is the endothelium basement membrane. All these layers are all conspicuously absent in Bruns et al. Also, since the source of collagen is not exclusively from the patient or a sterile genetically engineered source, the possibility of a gross immunologic reaction is significant.

Published U.S. Patent Application No. 88307687 to Werblin and Patel, describes a lens produced from a hydrogel material that is inserted under a corneal cap. As indicated in U.S. Pat. No. 4,505,855 to Bruns et al, dated Mar. 19, 1985, any material that is not identical to native tissue can and will affect optical clarity and diffusive capacity required for a healthy corneal structure.

Again, any means of producing a polymer implant which reduces the diffusion rate of oxygen, lipids, or aqueous media, reduces the effectiveness of the implant. Subtle changes in the intraocular pumping mechanism can cause significant loss in visual acuity. As before, nonnatural polymers can be rejected by the immune system.

Similar implants are revealed in prior art such as that described in European Patent No. 443,094/EP B1 to Kelman & DeVore. They utilize polymerized collagen material in conjunction with a periphery of fibrilized collagen. While providing improvements over simple collagen or other polymer implants, this suffers from the fact that the polymerized collagenous core does not contain fibrils at all as native tissue. Moreover, the fibrils on the periphery are not of the same diameter as in native tissue. As such, the permeability of the implant is low, thus affecting corneal hydration and overall nutritional levels. Further, since the collagen source employed can be derived from nonhuman sources, there is a susceptibility to immunologic effects.

European Patent No. 339,080/EP A1 to Gibson, Lerner, et al., reveals an improved prosthetic corneal implant in that the surface of the polymer is coated with crosslinked or uncrosslinked fibronectin. While this coating does improve epithelial adhesion, the problems of lack of diffusibility, optical clarity, and foreign body rejection are still present.

It is known to inject specialized gels in an effort to improve or change the radius of curvature of the cornea. U.S. Pat. No. 5,681,869 to Villain, et al., describes a biocompatable polyethylene oxide gel for injection into the cornea as a method of tissue augmentation. This procedure suffers from the fact that any gel lacks inherent structural integrity and thus can only augment existing tissue through limited hydrodynamic forces. Optical transmissibility and permeability are limited relative to material produced by the disclosed invention. Foreign body rejection is also possible.

Several prior art references disclose means of corneal repair through application of a suitable topographical ointment or solution. European Patent No. 778,021/EP A1 and Japanese Patent No. 8,133,968 JP to Ohuchi and Kato, disclose a solution of eye drops comprised of water, sodium chloride, potassium chloride, sodium bicarbonate, and taurine. This product suffers from the fact that as essentially a simple buffered isotonic saline solution, it is incapable of rendering any of the structural changes in the cornea required to correct high astigmatism, keratoconus, ectasia, burns, or corneal thinning. Further, the solution of Ohuchi and Kato is capable only of yielding temporary corneal surface relief due to minor, transient optical modifications.

European Patent Publication Nos. WO 00218441 and WO 00240242 to Bowlin & Wnek et al., published Mar. 7, 2002 and April 8$^{th}$ respectively, describe electrospun collagen fibers used a tissue scaffolds. Further, claims are made that the geometry of the electroprocessed matrix can be controlled by microprocessor regulation or by moving the spray nozzle with respect to the conductive target or vice versa. In reality, the electric charge that builds up on an electrospun fiber is significant, and results in whipping effect, which can vary fiber diameter and make precise deposition impossible as the fiber splays about the conductive target. This is because the DC high voltage source used in Bowlin et al., allows a like charge to accumulate on the fiber. As the fiber is ejected, a radius in the fiber will result in like charge repulsive forces to deflect the fiber in the opposite direction, where the radius decreases and the repulsive force increases. This process repeats itself, leading an uncontrolled ability to deposit material at a precise target and pattern. Further, the splaying about of the fibers results in tensile forces which varies the fiber diameter considerably.

The principal goal of the cited invention is to fabricate collagen constructs which serve as cell growth scaffold and to encourage neovascularization or blood vessel in growth. However, cell and vessel in growth are detrimental to a successful corneal collagen fibril structure and if allowed to transpire, would result in blindness. Finally, the precise fibril diameter and mean spacing between such fibrils in that construct necessary for corneal use is not described in Bowlin et al. And the lack of such exact fibril specification, uniform diameter, and matrix pattern would result in reduced optical transparency of the material and insufficient permeability for ocular use.

OBJECTS AND ADVANTAGES

The disclosed invention overcomes many of the limitations inherent in corneal transplants, solid polymer implants, mechanical implants employed to distort or reinforce the cornea, and much more, including the following:

(a) It provides a means of producing collagen polymer scaffolds in organized fibril strands at the same diameter as natural corneal stromal collagen, assuring the same optical clarity and diffusion characteristics as the original tissue. Significantly, this process permits additional tissue to be added to the cornea to augment structural integrity, therein correcting astigmatism, ectasia, failed LCAP, keratoconus, and other corneal problems.

(b) It affords a means of arranging collagen fibrils into a specific geometric matrix, which accurately mimics natural corneal stromal collagen.

(c) It teaches a means to affix the specialized collagen polymer matrix to the surrounding stromal tissue using glycerose, thereby precluding corneal cap displacement and enhancing the structural integrity of the stroma.

(d) It reduces or eliminates corneal nerve damage as a consequence of microkeratome corneal cap creation during LCAP or other similar corneal surgical procedures through the use of polyethylene glycol.

(e) It yields a means of producing a viable collagen polymer refractive correcting lens whose characteristics duplicate natural tissue and is capable of being integrated into and compatible with, the surrounding corneal collagen. This tissue is refractive and is ablatable for LCAP optimization.

(f) It teaches a means to create corneal collagen fibrils of the diameter, spacing, and pattern that mimics native tissue, necessary for proper transparency and hydration of the cornea.

Further objects and advantages will become apparent from a consideration of the ensuing description and accompanying drawings.

REFERENCE NUMERALS

Figure 1:
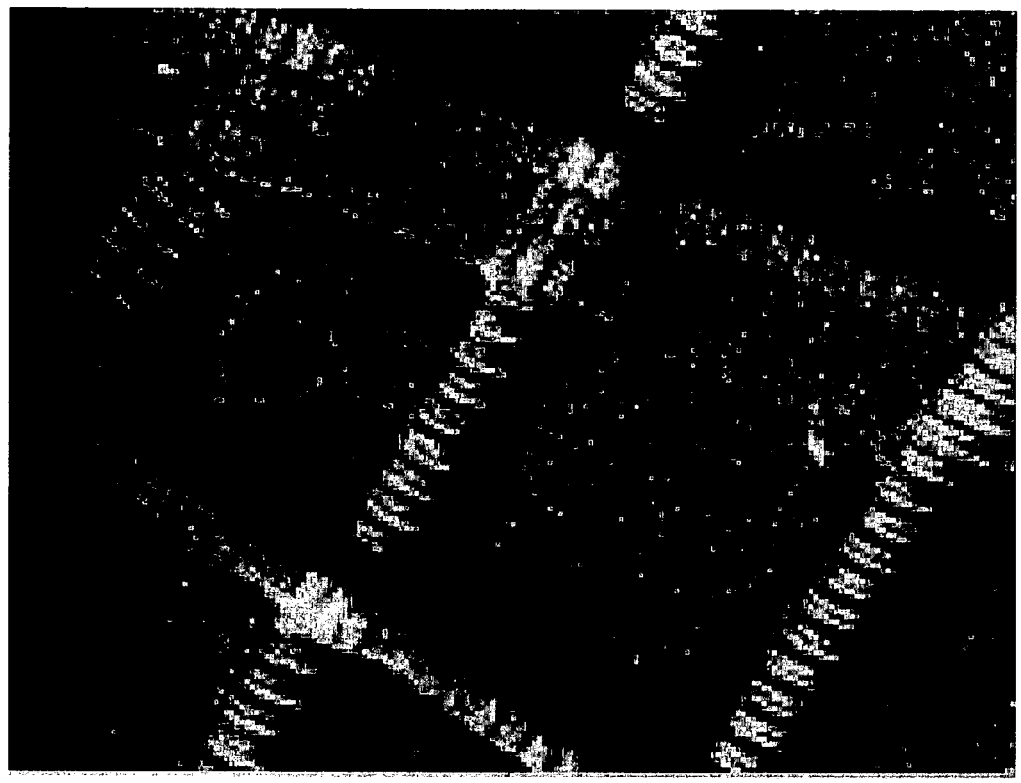
FIG. 1 is a detail characterization of human corneal stromal collagen fibrils obtained by a scanning electron microscope.

| REFERENCE NUMERALS | |
|---|---|
| 10 | Polymer Jet |
| 20 | Taylor Cone |
| 30 | Needle |
| 40 | Hydrostatic Pump |
| 50 | conductive target |
| 60 | Splaying Polymer Fibrils |
| 70 | Power Supply |
| 80 | Positive High Voltage |
| 90 | High Voltage Return-Ground |
| 100 | Table Displacement |
| 110 | Polymer Deposition Pattern |

PREFERRED EMBODIMENT

Figure 2:
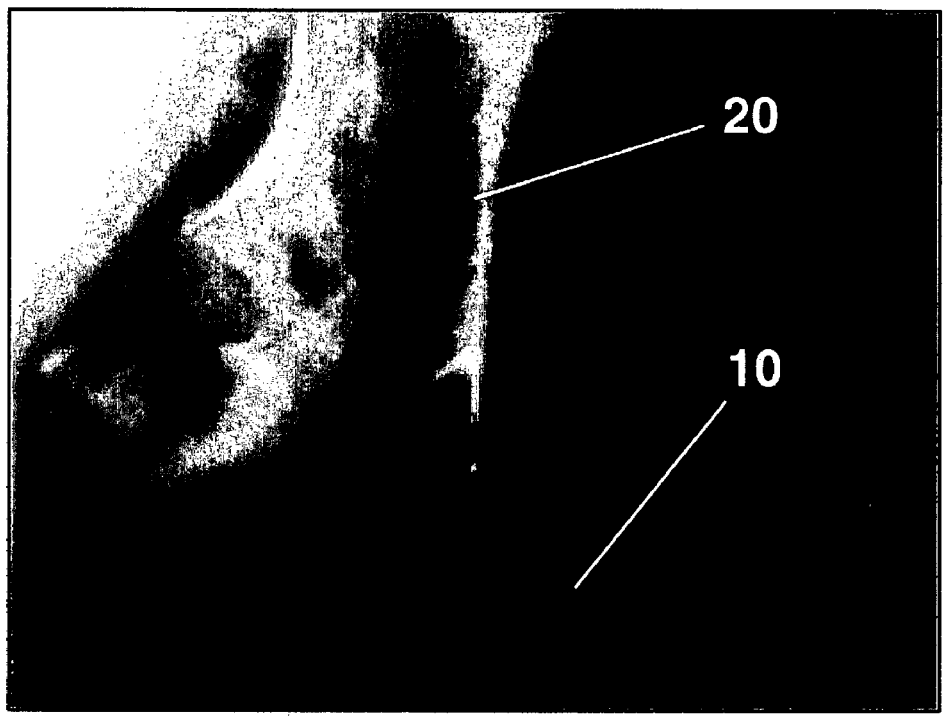
FIG. 2 is a characterization of an electrospray needle.
Figure 2:
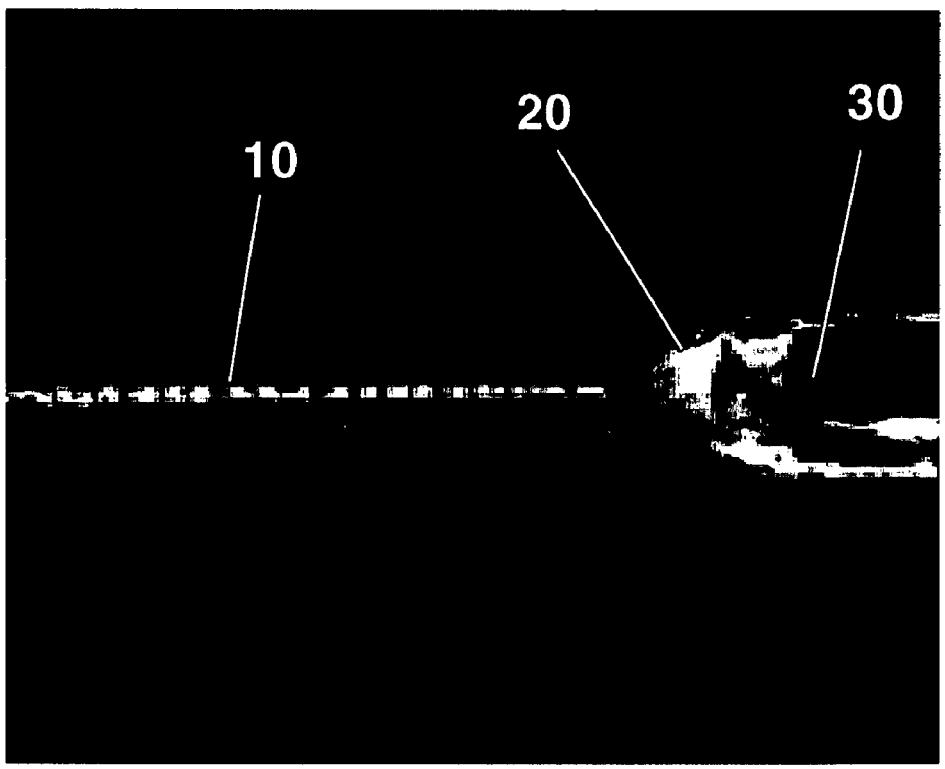
Figure 3:
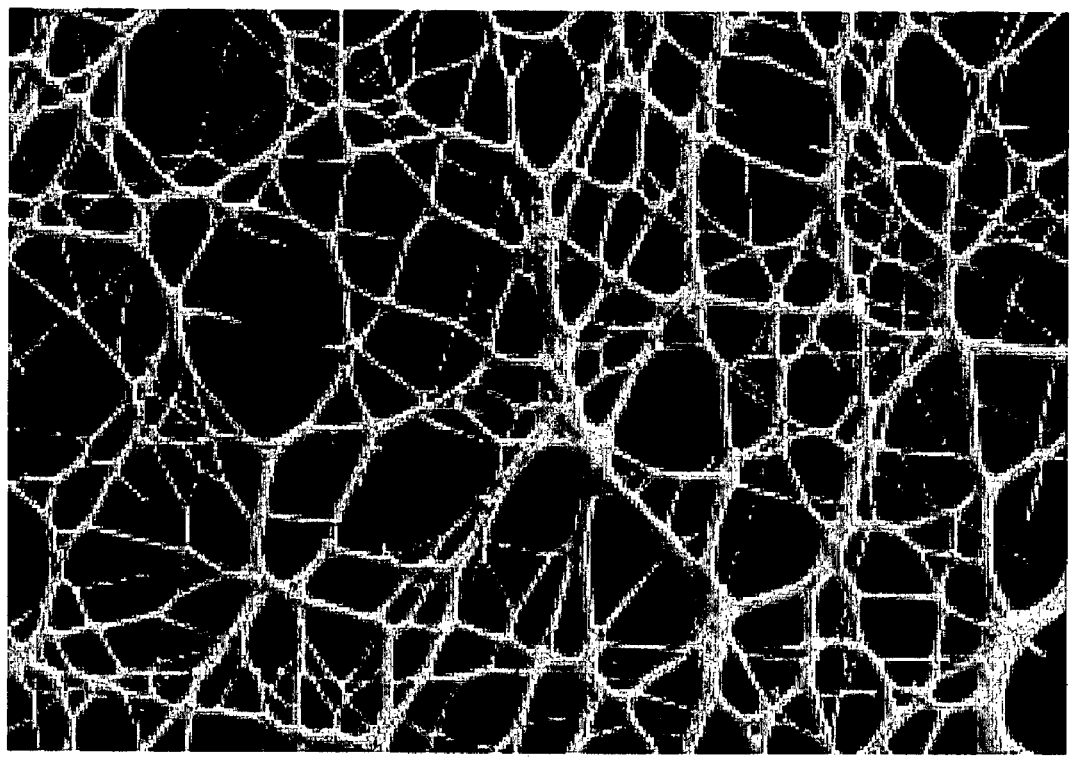
FIG. 3 is a schematic representation of a polymer pattern produced with a short source-to-target distance and with a high polymer concentration.
Figure 4:
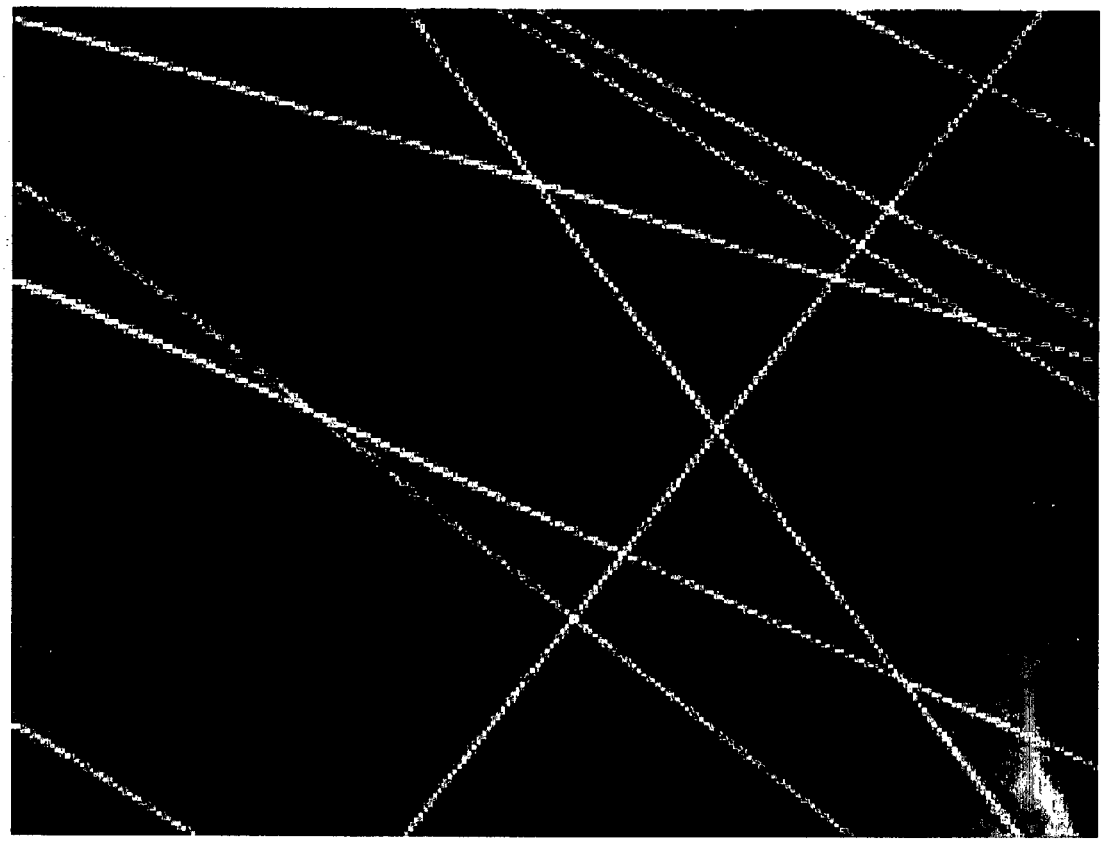
FIG. 4 is an illustration of fine collagen fibrils obtained by increasing source to target distance as opposed to that cited in FIG. 3.
Figure 5A:
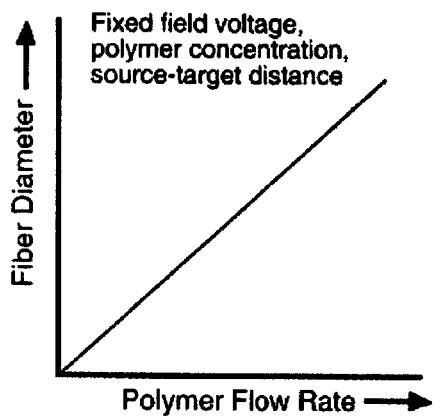
FIGS. 5A-5D are graphs that show Fiber Diameter as the dependent variable of independent variables Polymer Flow Rate, Polymer Concentration, Source- Target Distance, and Voltage respectively.
Figure 5B:
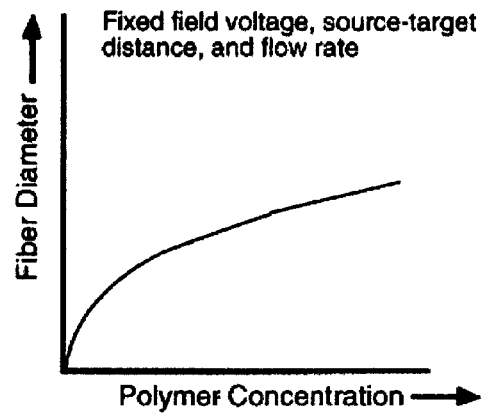
Figure 5C:
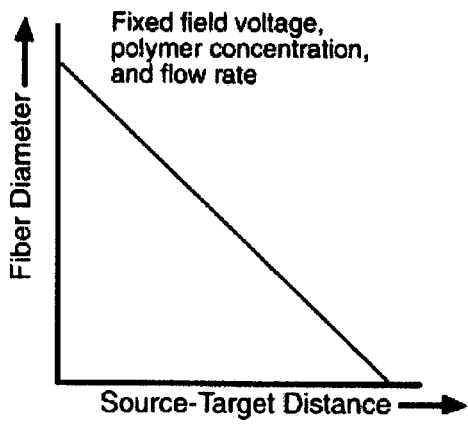
Figure 5D:
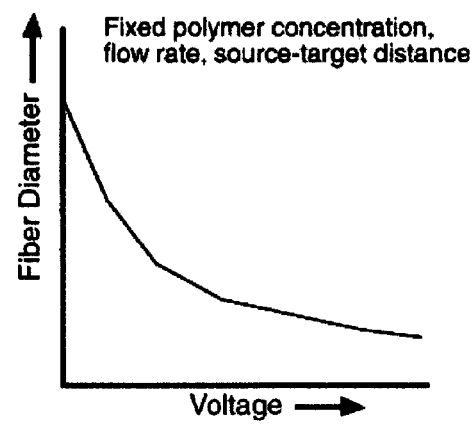

FIG. 1 illustrates in detail human corneal stromal collagen fibrils obtained by scanning electron microscopy. A preferred electrospray operation is illustrated in FIG. 2. An electrospray needle 30. The needle 30 supports a Taylor Cone 20 as a result of the electric field between the source needle 30 and an oppositely charged target or electrode. If the needle 30 were connected to a positive terminal 80 of a suitable high voltage supply 70, then the conductive target 50 would be the negative terminal 90. The resulting polymer jet 10 is produced at the apex of the Taylor Cone, and the jet 10 is attracted to and accelerates toward, the conductive target 50 electrode. The solvent evaporates during the flight from the source needle 30 to the conductive target 50, leaving behind a solid collagen fiber. The distance between the source needle 30 and the conductive target 50 may be reduced significantly if the electrospinning is performed in a bath of co-current or counter current gas flow, which serves to increase the evaporation of the solvent species. The same improvement in evaporation may be achieved if the electrospinning apparatus is placed in a suitable chamber under partial pressure. FIG. 3 illustrates a typical polymer pattern produced with a short source-to-conductive target distance and a high polymer concentration. FIG. 4 illustrates fine collagen fibrils by increasing source to target distance as opposed to that cited in FIG. 3. FIG. 5 identifies the conditions which affect electrospinning fibril diameter and fiber density.

Figure 6:
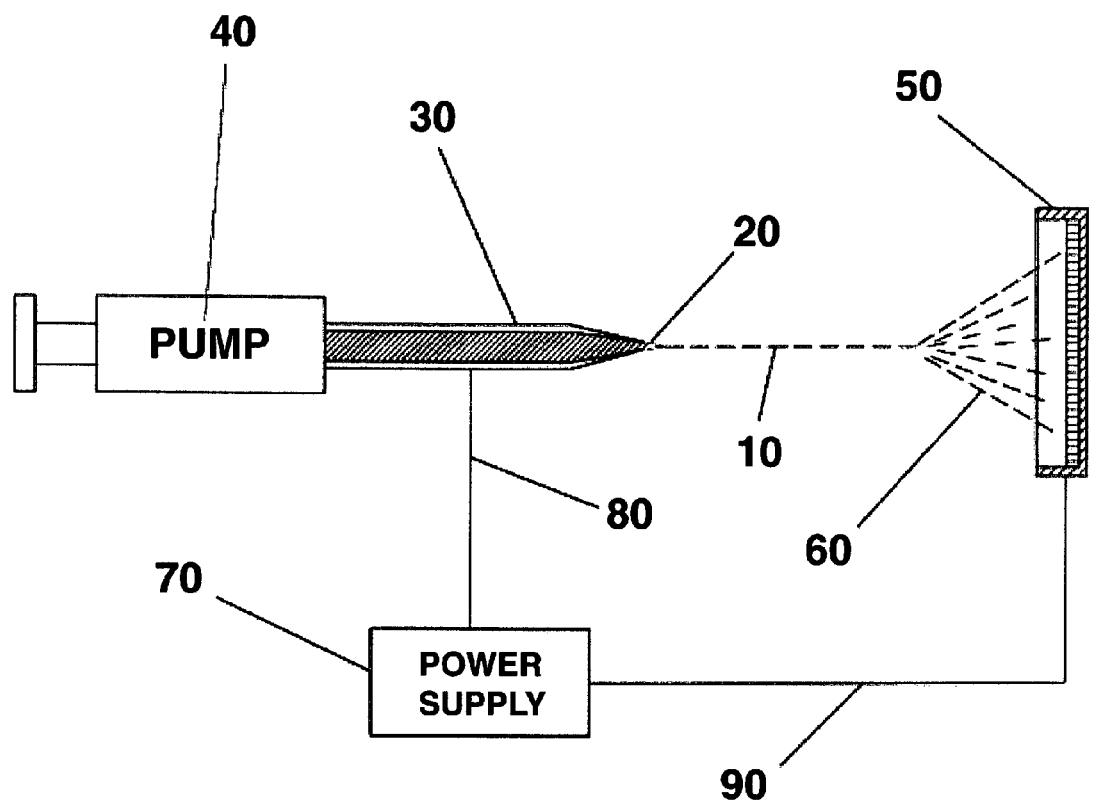
FIG. 6 is a schematic representation of a Hydrostatic Pump feeding polymer and solvent solution from a jet onto a collector-target.
Figure 7A:
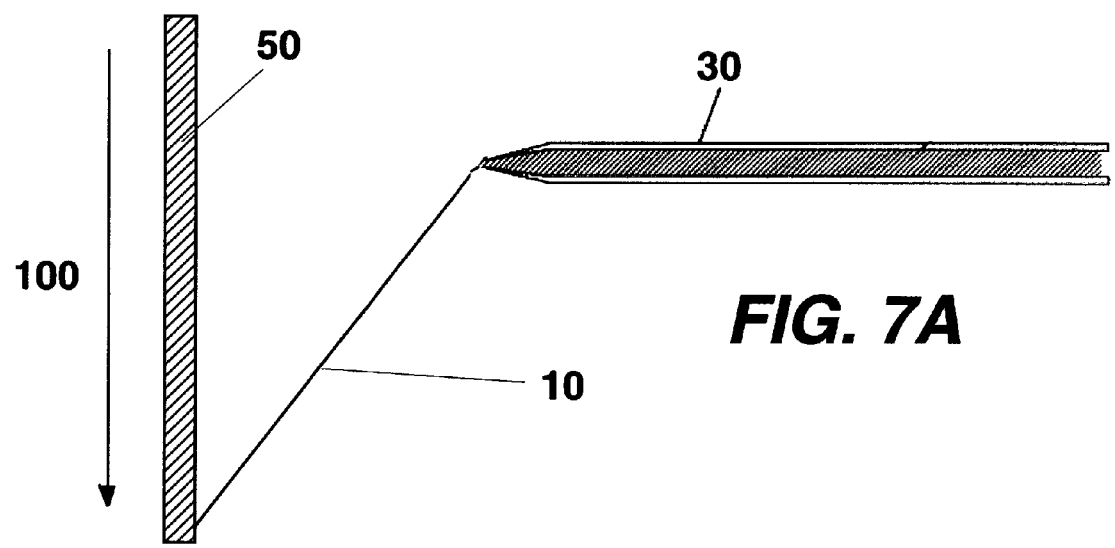
FIG. 7A is a schematic representation of a needle depositing electrospun polymer fiber Onto a collector-target.
Figure 7B:
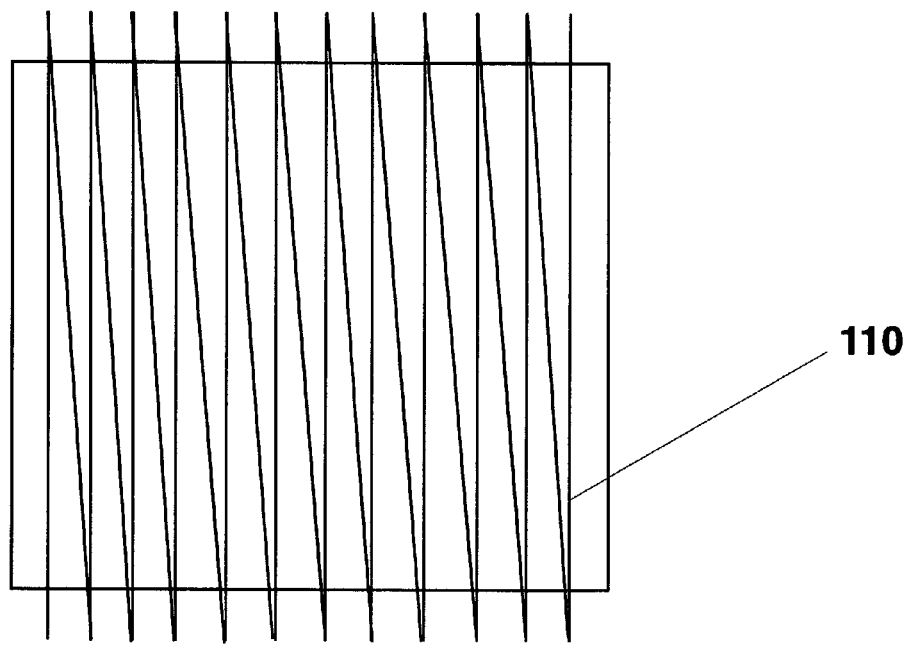
FIG. 7B is a schematic representation a stream of polymer fiber as it is deposited on a collector-target in a raster pattern.

A preferred embodiment of the collagen electrospinning process is illustrated in FIG. 6. A metering pump 40 exerts hydrostatic pressure on a collagen solution. Alternating current at a high voltage preferably between 1,000 and 20,000 volts at terminal 80, creates an electrostatic field between the source needle 30 and the conductive target 50, a screen. At the tip of the syringe needle, a Taylor cone 20 is formed which emits a fine polymer jet 10 that expands outward to produce a filament 60 and deposited on target 50. FIG. 7 depicts the creation of an electrospun orthogonal matrix, achieved by fixing either needle 30 with respect to a moving conductive target 50, or vice versa. When emitting jet 10, the source or conductive target is displaced linearly until maximum coverage is achieved, at which point the direction is reversed and the process repeated, effectively "scanning" over conductive target range 100. This process is duplicated in the alternate axis by rotating the target orthogonally. A regular matrix 110 can thus be created. A final polymer "mat" is cut by several means, preferably by laser trimming.

It is imperative that in order to form collagen fibrils of the correct diameter, preferably 65 nm, and the correct mean distance, preferably 300 nm that the charge on the fiber due to the electric field be neutralized. If DC is used as a high potential source, the distributed charge will result in repulsive forces which bend the fiber being spun. This bending or whipping action repeats since like charges repel, and arc in the fiber brings these like charges closer together forcing the fiber violently in the opposite direction. The violent motion of a charged fiber exerts significant tensile loads on the fiber itself, pulling the fiber into a smaller diameter. (Use of a DC power supply may be acceptable if the charge on the fiber is removed by other means, such as through the use of a high voltage field emission electron source, an AC or DC corona discharge, ultraviolet light source, radioactive ion generator).

Therefore, accurate and repeatable fibril diameters cannot be achieved without steps being taken to minimize charge build-up on the fibril strands as they reach the target in the Taylor cone deposition process. While un-controlled charge build-up and whipping does not present it self as a problem for tissue scaffolding, controlled fibril diameter, deposition density, and interfibril spacing are critical parameters if a successful corneal tissue is to be achieved. Fibers that are too large in diameter will diffract incident light, making the material less transparent. If the fibers are too close together or the density of the fibril mat too great, the diffusion properties of the resulting electrospun mat will be impaired, possibly resulting in blindness.

The disclosed invention provides a means to augment existing corneal tissue, adding refractive material which can be subjected to LCAP optimization. It further enhances the structural integrity of weak cornea by providing an additional collagen matrix to existing tissue and by the use of glycerose, which cross links the collagen polymer to existing tissue. The disclosed invention is not a tissue scaffold in the traditional sense. That is, the collagen fibrils produced by the disclosed invention do not encourage cellular in growth or neovascularization, both of which would defeat the purpose of use in the eye by occluding light and reducing permeability of the corneal structure.

A particular object of the invention is to provide a means of restoring to normal corneas' whose surface has been damaged by trauma, failed LCAP, burns, and other mechanical disruptions, so that optical distortion, and/or reduction of transparency is reduced or eliminated. Diseases that impact the cornea include keratoconus, keratoglobus, pellucid marginal degeneration, and corneal dystrophies. The potential to either augment (as in keratoconus) or replace (as in corneal dystrophies such as Fuch's Endothelial Dystrophy) corneal tissue is the object of this invention.

Still other objectives and possible applications of the invention will become evident to those knowledgeable in the related arts. The first of which is the ability to create a natural corneal refractive lens to be implanted into existing stromal tissue.

The following example illustrates the practice of the invention in a preferred embodiment. The disclosed procedure offers a means of reconstructing corneal tissue, rebuilding stromal integrity, and corneal reshaping by laser surgery. According to the present invention, a process known as "electrospinning" is used to produce human collagen, preferably Type I (Type I is the principal component of bone, skin, and tendon), in micro strands that approximate or match the nanometer size fibrils of natural human corneal stromal collagen. The fibril diameter is regarded as the principal factor in achieving corneal transparency, as does the mean distance between fibrils. The fibril strands are deposited onto an appropriate conductive target 50, which allows a collagen fibril mat to develop. The density and configuration of this mat determine the permeability of the structure to aqueous fluids, lipids, and gases, as well as the ultimate optical transparency. The density and orientation of these fibrils, illustrated in the drawings, are controlled in order to achieve the desired diffusive and optical parameters compatible with natural tissue. The resulting sheet or pad of collagen fibers can be trimmed to the desired dimensions and can either be inserted under a corneal cap during normal LCAP surgery to prevent ectasia (a distension of the cornea due to thinning), or can be placed as an corneal overlay to add structural reinforcement to the cornea in treating such disorders as keratoconus. Or, it can be used either intracorneally or topically as a refractive correcting contact lens which can absorbed and integrated into the native corneal stromal tissue.

The Corneal Stroma

The principal structural material of the cornea is collagen; as indicated, its particular organization accounts for the transparency of the stroma. In the human cornea, collagen fibers have a uniform diameter and regular spacing between them. The fibers and the keratocytes between them are oriented in parallel to form lamellae (or layers). The lamellae are superposed with others in a regular order, the collagen in each lamella being perpendicular to the adjacent lamellae. An important factor in transparency is the hydration of the proteoglycans (non-collagenous component of a cartilage matrix). This determines the regular spacing of the collagen fibers and the distance between the fibers. The principal keratan sulfate proteoglycans are lumican, keratocan, and mimecan.

The galactosaminoglycans rich proteoglycans (chondroitin sulphate, dermatan sulphate, and keratan sulfate) that are expressed in the stroma have a high water affinity. Their water affinity is counterbalanced by the pump mechanisms in the endothelial cells. Proteoglycans also play a role binding the growth factors, and act as adhesive proteins. The differentiated connective tissue in the stroma contains 80% to 90% of water on a weight basis. Collagen, other proteins, and glycosaminoglycans of mucopolysaccharides constitute the major part of the remaining solids. Corneal fibrils are neatly organized and present the typical 64 to 66 nanometer periodicity of collagen. These collagen fibrils form the skeleton of the corneal stroma. The physicochemical properties of corneal collagen do not differ from those of tendon and skin collagen. Like collagen from these other sources, corneal collagen is rich in nitrogen, glycine, proline, and hydroxyproline. Mucopolysaccharides (MPS; glycosaminoglycans) represent 4% to 4.5% of the dry weight of the cornea. MPS are localized in the interfibrillar or interstitial space, probably attached to the collagen fibrils or to soluble proteins of the cornea. The MPS in the interstitial space play a role in corneal hydration through interactions with the electrolytes and water. Three major MPS fractions are found in the corneal stroma: keratin sulfate (50%), chondroitin (25%), and chondroitin sulfate (25%). The interstitial fibril structure must allow the MPS to flow freely, in concert with water and oxygen. All of this is necessary to promote corneal health, mechanical integrity, and optical clarity.

Creating Replacement Corneal Stromal Collagen Fibrils

Transparent stromal structures that can be implanted into a recipient cornea to augment or replace existing tissue are fabricated according to the present invention. It further permits creation of specialized collagen that integrates itself with the existing surrounding tissue to form a single fully functional stroma. Additional benefits include in vitro creation of complete.

In order to provide a suitable stromal structure, fibrils of collagen, again, preferably Type I, must be created and layered to form the mat which exhibits the transparency and diffusion characteristics of healthy tissue. In the preferred embodiment, an electrospinning process produces the collagen fibrils. In this technique, the polymer under consideration, in this case the collagen solute, is dissolved by a suitable solvent and injected under hydrostatic pressure into a conductive needle or capillary. An AC or DC potential of preferably 4,000 to 12,000 volts is maintained between injection needle and a suitable conductive target away from the needle at a distance sufficient to preclude production of a corona or arc. The voltage is adjusted according the distance and desired fiber diameter and structure. The voltage difference between the injection needle and the conductive target needle and suited to the given solvent conductivity, polymer, and flow rate, the resulting electrostatic field at the needle tip results in the formation of what is known as a Taylor Cone. (G. I. Taylor first described how a polarizable liquid under the influence of an electric field would form a meniscus which is a cone. Proced. Royal Society, vol. 313, pp. 453, 1969.) When the field is increased, a fluid jet is emitted from the tip. Evaporation of solvent from this jet results in a polymer strand of collagen. This strand is attracted to, and impacts with, the ground cathode target. The accumulation of such strands creates a the mat of collagen fibers having a diameter ranging from tens of microns or more down to tens of nanometers or less, depending upon the concentration and nature of solute, the conductivity and viscosity of liquid, and the potential difference between the needle and conductive target 50 conductive target flap on the patient's conductive target globe. It has been shown by Wnek et al. of Virginia Commonwealth University (VCU) in Biomacromolecules, 2002, Vol. 3, pp. 232-238, that electrospun collagen fibers can be produced down to 100+/−40 nano meters in diameter. Calf skin dissolved in a suitable solvent was electrospun, and upon transmission electron microscopy (TEM) examination, revealed the same banded appearance characteristic of native polymerized collagen. Various polymers studied yielded fiber diameters in the range of 0.1 to 10 um. Extrusion, where a polymer such as collagen is drawn through an orifice, rather than electrospinning, is an alternative in certain instances. Evaporation of solvent from this jet results in a polymer strand of collagen. A co-current or counter current gas flow, preferably with nitrogen, can improve the solvent evaporation so that the distance between the spray needle and conductive target and the applied voltage may be reduced, permitting more accurate fiber deposition control.

Collagen mats produced by this process can have diameters up to tens of millimeters and thicknesses of up to hundreds of microns, depending upon deposition time. Similarly, collagen for creating a suitable corneal can be derived from a variety of sources. In the preferred embodiment, synthetic collagen such as that manufactured by FibroGen of San Francisco, Calif., is dissolved by a solvent such as 1,1,1,3,3,3 hexaflouro-2-propanol (HFIPA) and electrospun into a fibril diameter of preferably 65 nanometers, +/−50 nanometers with a mean distance between fibers of preferably 300 nm, and layered into a mat that can be trimmed to desired final dimensions. Again, extrusion rather than electrospinning of the polymer is an alternative in certain instances). Laser cutting is often employed since fibril terminations must be severed and should not be excessively frayed or tangled. Tangling or fraying can affect bonding to native collagen and can vary optical transparency. While the resulting collagen mat consists of disorganized fibrils, this does not interfere with required transparency or diffusion characteristics. The general theory for corneal transparency has to do with the diameter of the collagen fibers in reference to the wavelength of the incident light. Organization of the fibers appears to be of less importance, however, the mean distance between fibrils must be controlled. This conclusion is supported by the fact that shark cornea exhibits regions of disorganized but roughly equally spaced fibers with random interfibrillar distances, yet exhibit a high degree of optical transparency. Use of alternating current microspun collagen fibers allows precise control of the fibril diameter. The deposition rate determines the interfibrillar spacing.

An alternative source of suitable corneal collagen is the autologous transplantation of patient collagen derived from biopsy from a region or regions elsewhere in the body. A useful source can be derived from pluripotent stem cells from bone marrow. The marrow contains several cell populations, including mesenchymal stem cells that are capable of differentiating into adipogenic, osteogenic, chondrogenic, and myogenic cells. Bone marrow procurement has obvious limitations, such as extreme discomfort for the patient during harvesting, thus an alternative source is desirable. One source found by Zuk et al., includes autologous stem cells from human adipose tissue obtained by suction-assisted lipectomy or liposuction. Grown in vitro, a fibroblast-like population of cells or a processed lipoaspirate, which differentiate into adipogenic cells that produce collagen. Such cultured cells are then dissolved as previously described and electrospun or extruded for corneal use.

Electrospinning Controlled Corneal Collagen Fibril Matrices

Modification of the electrospinning process to yield a cross hatch pattern is achieved by maintaining either the needle anode fixed and moving the conductive target, or vice versa. Under normal conditions, the electrospun collagen fiber is splayed about by the interplay of mechanical, hydrodynamic, and electrical forces so as to cause the polymer strands to accumulate on the conductive target in a random pattern. While ordinarily this is not a problem in stromal scaffold mat construction, since the fiber diameter is the principal factor in corneal transparency, there are instances where a regular matrix of stromal collagen is desired. By rapidly moving the needle in a linear direction for a fixed distance and then reversing such motion with respect to the conductive target, while at the same time indexing the conductive target utilizing a stepper motor drive or piezo stack or other such precision positioner, a series of relatively straight and parallel fibers may be laid down on the conductive target. After the desired pattern has been achieved in one axis, the conductive target may be rotated ninety degrees and the process repeated.

The outer fringes of a collagen mat matrix so created will be less organized than the central axis as the outer edge is where conductive target position reversal occurs. However, this area can be trimmed away and discarded with a suitable laser. The resulting central scaffold area exhibits a collagen structure, pattern, and diameter that closely mimics natural stromal collagen. If even greater accuracy is required in fibril spacing, the distance the fiber is deposited across a moving conductive target can be increased and the jet shut down at the point of maximum travel. The conductive target is then indexed to the next position, the electrospinning jet reestablished, and the conductive target rapidly moved to the opposite extreme, where the process is repeated until the maximum linear coverage area of fibers in one axis of orientation is achieved. The conductive target may then be rotated ninety degrees as before and the spinning procedure repeated.

Improvements to the electrospinning process include utilizing a source of free ions generated electrically or from a suitable radioactive source, to neutralize the charge on the surface of the polymer jet to minimize Coulomb repulsion and thus the extent of splaying. In addition, alternating the jet high voltage polarity at high frequency can decrease or eliminate fiber charging so that precise fiber deposition may be achieved.

Inserting the Replacement Collagen Tissue

After the fabricated microspun or extruded collagen fibril scaffold is produced, it is preferably laser trimmed into the desired diameter and thickness required for a given recipient. The recipient is preferably treated with pharmaceuticals used to treat glaucoma which reduce the intraocular pressure prior to the operative procedure. Employing epithelial debridement, epithelial placement to the side (such as in the LCAP procedure), or creation of a corneal conductive target globe the newly grown corneal cellular sheet is placed over the denuded corneal stroma. Orientation of an organized parallel fibril corneal sheet and the existing natural fibril structure, if required, may be accomplished by utilizing a polarized light and rotating the applied collagen sheet until a similar interference pattern is achieved. Glycerose is then applied to initiate collagen crosslinking between the corneal tissue and the corneal sheet, thereby providing an adhesive.

If a flap has been created during LCAP, additional glycerose is added before the flap is dropped, covering the repair. Further, the use of glycerose assists in maintaining corneal flap position during healing. Since adding collagen tissue may affect corneal flap suction when such a flap is replaced because overall corneal thickness will increase, glycerose-initiated crosslinking will secure the flap and added tissue in place, preventing a lost corneal cap. Further glycerose treatment also minimizes or eliminates the possibility of corneal wrinkles or striae. An added benefit is that glycerose use actually increases the mechanical integrity of the cornea. Experiments with rabbit eyes have shown that corneal transparency is lost when intraocular pressure is increased, but such is not the case with corneas similarly tested that have been previously treated with glycerose. This fact alone holds great promise in effecting interstitial bonding that we believe can keep keratoectasia (thinning of the cornea leading to distension and reduced vision) from occurring. The use of glycerose also minimizes epithelial ingrowth.

Finally, the combination of glycerose with polyethylene glycol or the use of polyethylene glycol alone can also be employed to assist in nerve repair when a corneal flap has been created. There is evidence to support the view that nerves severed in healthy corneas dull sensations necessary to effect the so called blink response, thereby potentially causing dry-eye syndrome. The resulting decrease in lubrication can damage the epithelial layer, increase the potential for ocular infection, and reduce visual acuity. Polyethylene glycol (PEG) has been shown to permit healing of recently severed nerves elsewhere in the body, particularly for spinal nerves, but has not been reported in the literature utilized for prevention of dry eye syndrome or any other ocular use.

After about three days, epithelial cells cover the repair site. The drugs employed to reduce the intraocular pressure are now discontinued and the healing tissue is allowed to stabilize over a period of three to six months. Corneal topographical data, wavefront measures of higher order aberration, and other refractive measurements are then obtained and laser reshaping subsequently performed to effect final refractive correction.

We claim:

1. A method of producing a controlled corneal collagen fibril matrix with a controlled cross-hatch pattern of fibril strands of collagen on a conductive target for transfer to a cornea, comprising the steps of:
   A) providing a conductive spraying needle having a conductive needle tip, and a conductive target,
   B) forming a solution of collagen using a solvent, and loading the solution of collagen in the conductive spraying needle having a conductive needle tip,
   C) providing a power source having an alternating output voltage adjustable over a range extending from 1000 to 20,000 volts, the output voltage being coupled to produce an electric field between the conductive target and the conductive needle tip,
   D) adjusting the alternating output voltage of the power source to produce a strand of collagen fiber from a Taylor Cone from the solution of collagen passing from the conductive needle tip to the conductive target when the electric field exceeds the surface tension of the solution of collagen fluid in the conductive needle tip,
   E) directing the strand of collagen fiber from the Taylor Cone onto the conductive target from the conductive needle tip,
   F) moving said conductive spraying needle having a conductive needle tip in a linear direction for a fixed distance and then
   reversing such motion with respect to said conductive target while at the same time indexing the target utilizing a precision positioner, to deposit a first collagen mat of collagen fibril strands laid down on said conductive target, and then
   rotating the target ninety degrees and repeating the process to obtain a second mat of collagen fibril strands laid down on said first collagen mat of collagen fibril strands on said conductive target, the first and second mat forming a controlled corneal collagen fibril matrix with a controlled cross-hatch pattern,
   G) evaporating said solvent from said controlled corneal collagen fibril matrix with a controlled cross-hatch pattern on said conductive target,
   H) repeating steps E-G to obtain
   the controlled corneal collagen fibril matrix with a controlled cross-hatch pattern of collagen fibril strands having a thickness sufficient for transfer to a cornea.

2. The method of claim 1, further comprising:
   adding step I to follow step H wherein step I comprises:
      transferring the controlled corneal collagen fibril matrix with a controlled cross-hatch pattern of collagen fibril strands-having a thickness sufficient for transfer to a cornea into the cornea of a living human.

3. The method of claim 1 wherein step E includes the step of exposing the strand of collagen fiber from the Taylor Cone passing from the conductive needle tip to the conductive target to ionizing radiation.

4. The method of claim 2 wherein step I comprises the steps of:
   I-1 laser trimming the controlled corneal collagen fibril matrix with a controlled cross-hatch pattern of collagen fibril strands having a thickness sufficient for transfer to a cornea to the desired diameter and thickness required before transfer of the controlled corneal collagen fibril strands matrix to a patient's corneal globe,
   I-2 surgically creating a corneal flap on the patient's corneal globe,
   I-3 positioning the laser trimmed controlled corneal collagen fibril matrix with a controlled cross-hatch pattern of collagen fibrils over the denuded corneal surface,
   I-4 dropping the flap over the controlled corneal collagen fibril matrix with a controlled cross-hatch pattern of collagen fibrils to complete a repair procedure.

5. The method of claim 1 wherein step E further comprises the step of applying a source of free ions from an ionizing source to the strand of collagen fiber from the Taylor Cone passing from the conductive needle tip to the conductive target to neutralize any distributed charge on the collagen fibril strands.

6. The method of claim 5 where the ion source is electrically generated.

7. The method of claim 5 where the ionizing source is an ultraviolet light.

* * * * *